United States Patent [19]

Wang

[11] Patent Number: 4,489,011
[45] Date of Patent: Dec. 18, 1984

[54] HYPOGLYCEMIC N-(2-SUBSTITUTED-3-DIALKYLAMINO-2-PROPENYLIDENE)-N-ALKYLALK-ANAMINIUM CAMSYLATE SALTS

[75] Inventor: Samuel S. M. Wang, Indianapolis, Ind.

[73] Assignee: Merrell Dow Pharmaceuticals Inc., Cincinnati, Ohio

[21] Appl. No.: 494,742

[22] Filed: May 16, 1983

[51] Int. Cl.³ .................................... C07C 143/20
[52] U.S. Cl. .................... 260/501.19; 260/501.2; 424/316
[58] Field of Search ............. 260/501.19, 501.2

[56] References Cited

FOREIGN PATENT DOCUMENTS 2317230 10/1973 Fed. Rep. of Germany .

OTHER PUBLICATIONS

B. Rada, A. Luczak, A. Holy and Z. Arnold., Chemotherapy 20, 141-7, (1974).
C. Jutz, R. Kirchlechner and H. J. Seidel, Chem. Ber. 102 (7), 2301-18, (1969).
A. Holy and Z. Arnold, Coll. Czech. Chem. Commun. 38(5), 1371-80, (1973).
Z. Arnold, Coll. Czech Chem. Commun. 38(4), 1168-72, (1973).
C. Jutz, R. M. Wagner and H. G. Loebering. Angew. Chem. Int. Ed. in English 13, 737-9, (1974).
C. Jutz and E. Schweiger, Chem. Ber. 107(7), 2383-96, (1974).
C. Jutz, R. M. Wagner, A. Kraatz and H. G. Loebering, Justus Liebigs Ann. Chem. 1975(5), 874-900.
C. Jutz and H. G. Peuker, Synthesis 1975(7), 431-3.
H. Lee, N. Shyamasundar and R. G. Harvey, J. Org. Chem. 46(4), 2889-95, (1981), CA 95: 42748s.
C. Jutz, H. G. Loebering and K. H. Trinkl, Synthesis 1977(5), 326-8.

*Primary Examiner*—Nicky Chan
*Attorney, Agent, or Firm*—Edlyn S. Simmons; Gary D. Street; Raymond A. McDonald

[57] ABSTRACT

Camsylate salts of N-(3-dialkylamino-2-propenylidene)-N-alkylalkanaminium substituted in the 2-position with an ether or thioether and having the formula

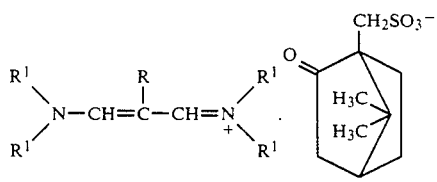

are active as hypoglycemic agents.

4 Claims, No Drawings

HYPOGLYCEMIC N-(2-SUBSTITUTED-3-DIALKYLAMINO-2-PROPENYLIDENE)-N-ALKYLALKANAMINIUM CAMSYLATE SALTS

BACKGROUND OF THE INVENTION

Hyperglycemia, an abnormally elevated level of blood sugar, is the primary symptom of diabetes mellitus, a metabolic disease characterized by inadequate response to insulin or inadequate secretion of insulin from the islets of Langerhans of the pancreas. Control of elevated blood sugar levels may be achieved through injection of insulin or by administration of pharmaceutical hypoglycemic agents, usually by the oral route. The majority of known hypoglycemic agents are sulfonylureas, such as chlorpropamide and tolazamide, and biguanides, such as phenformin.

It has now been discovered that certain N-(2-substituted-3-aminopropenylidene)alkanaminium salts are active as oral hypoglycemic agents. Several of these compounds are known to the prior art as the perchlorate salts. With the exception of a study by Rada, et al., (Chemotherapy 20, 141–7 (1974)). in which N-(3-(dimethylamino)-2-ethoxy-2-propenylidene)-N-methylmethanaminium perchlorate was tested unsuccessfully for antiviral activity, however, it has not previously been suggested that the N-(2-substituted-3-aminopropenylidene)alkanaminium salts have any biological activity.

SUMMARY OF THE INVENTION

The present invention relates to novel N-(2-substituted-3-amino-2-propenylidene)alkanaminium camsylate salts of general formula I

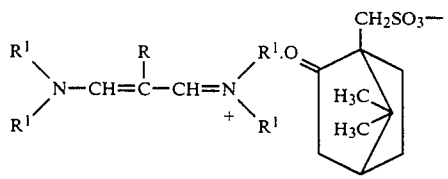

wherein R represents a group of formula $R^2X$; $R^1$ represents methyl or ethyl; $R^2$ represents straight or branched alkyl of from 1 to 12 carbon atoms, straight or branched alkenyl of from 2 to 12 carbon atoms, cycloalkyl of from 3 to 8 carbon atoms, cycloalkylalkyl of from 4 to 10 carbon atoms, optionally substituted phenyl or benzyl; and X is an oxygen atom or a divalent sulfur atom.

The novel camsylate salts are useful in the method of lowering blood sugar in a hyperglycemic mammal which is disclosed and claimed in an application Ser. No. 494,741 entitled Hypoglycemic N-(2-Substituted-3-Dialkylamino-2-Propenylidene)-N-Alkylalkanaminium Salts of Eugene R. Wagner, Charlotte L. Barney and Donald P. Matthews, filed on even date herewith.

The camsylate salts of the present invention have desirable solubility, high stability properties, nonhygroscopicity and superior palatability when compared with other salts of the corresponding alkanaminium cations.

DETAILED DISCLOSURE OF THE INVENTION

As used herein, the term alkyl embraces straight and branched chain alkyl moieties of from 1 to 12 carbon atoms, for example, methyl, ethyl, propyl, isopropyl, n-butyl, 1-methylpropyl, n-pentyl, 3-methylbutyl, n-hexyl, n-heptyl, 3-ethylpentyl 1-methylundecyl and n-octyl. Optionally substituted phenyl refers to unsubstituted phenyl, to phenyl substituted by from one to three groups selected from lower alkyl, lower alkoxy, halogen, hydroxy, benzyloxy, di(lower alkyl)amino, nitro, phenyl or benzyl, wherein lower alkyl and lower alkoxy include straight and branched alkyl chains of from 1 to 4 carbon atoms and halogen includes bromine, chlorine, fluorine and iodine, and to phenyl substituted by a single 2,3- or 3,4-methylenedioxy moiety.

The compounds are salts of 10-camphorsulfonic acid, i.e., 2-oxo-10-bornanesulfonic acid.

Compounds of the present invention are suitable for treatment of diabetes mellitus or for lowering elevated blood glucose levels resulting from other disorders, such as pancreatitis. They may be administered alone or in compositions incorporating art-recognized excipients by the oral, subcutaneous, intravenous or intraperitoneal route. The compounds are especially advantageous when administered orally.

As disclosed in the above-referenced application of Eugene R. Wagner, et al., filed on even date herewith, methanaminium salts of formula Ia

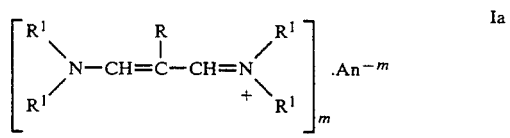

wherein R represents a group of formula $R^2X$; $R^1$ represents methyl or ethyl; $R^2$ represents straight or branched alkyl of from 1 to 12 carbon atoms, straight or branched alkenyl of from 2 to 12 carbon atoms, cycloalkyl of from 3 to 8 carbon atoms, cycloalkylalkyl of from 4 to 10 carbon atoms, optionally substituted phenyl or benzyl; X is an oxygen atom or a divalent sulfur atom; An is a pharmaceutically acceptable anion; and m represents the valence of the anion; are useful as hypoglycemic agents when administered orally or parenterally.

Formulation of suitable dosage forms for administration of compounds of general formula Ia is limited by their physical characteristics. Conventional salts of formula Ia have been found to be highly hygroscopic, rendering difficult the preparation of solid pharmaceutical dosage forms having uniform characteristics and stability. Perchlorate and nitrate salts are potentially explosive, further complicating the preparation and storage of suitable dosage forms. In addition, chronic therapy of elevated glucose levels requires that the alkanaminium salts of general formula Ia employed therein bear an anion which is not itself physiologically active, in order that unacceptable side effects will not occur by virtue of the physiological activity of the anion.

The novel camsylate salts of general formula I present none of these disadvantages. The camsylate salts of general formula I are neither hygroscopic nor explosive, rendering them suitable for the preparation of conventional solid dosage forms with acceptably long shalf lives. The camsylate anion is physiologically inert and thus introduces no unwanted side effects during long term administration. In addition, the camsylate salts of general formula I have an agreeable taste, rendering them highly acceptable for oral administration.

The hypoglycemic activity of the novel camsylate salts of general formula I compares favorably with that of the corresponding salts of general formula Ia bearing conventional pharmaceutically acceptable anions.

The effective hypoglycemic amount of the active compounds to be internally administered to a mammal, that is the amount which is effective to significantly lower the amount of sugar in the blood, can vary depending upon such factors as the particular N-(2-substituted-3-amino-2-propenylidene)alkanaminium camsylate salt employed, the severity of the disease, the desired level of blood sugar to be obtained, the period of administration and the method of administration. In general, an effective daily dosage range is from about 1 to about 750 mg/kg of body weight with a daily dosage range of from about 50 to 500 mg/kg of body weight, in a single or divided oral dose, being preferred. Suitable dosage forms may be prepared by following the conventional techniques of the pharmacist. The compounds of general formula I together with suitable pharmaceutical carriers can be in the form of conventional solid unit dosage forms such as tablets or capsules, or embedded in a polymeric matrix for sustained release. In solid unit dosage forms the compounds can be combined with conventional carriers, for example, binders, such as acacia, corn starch or gelatin; disintegrating agents, such as corn starch, guar gum, potato starch or alginic acid; lubricants, such as stearic acid or magnesium stearate; and inert fillers, such as lactose, sucrose, corn starch, cellulose, or synthetic polymers, such as polyvinylpyrrolidone.

The compounds of general formula I may also be administered as liquid suspensions or solutions using a sterile liquid, such as an oil, water, an alcohol, or mixtures thereof, with or without the addition of a pharmaceutically suitable surfactant, suspending agent, or emulsifying agent. Water, saline, aqueous sucrose and related sugar solutions, alcohol and polyethers such as glycerol, and polyethers, such as polyethyleneglycol, may be employed in the preparation of liquid formulations which may suitably contain suspending agents, such as pectin, carbomers, methyl cellulose, hydroxypropyl cellulose or carboxymethyl cellulose, as well as buffers and preservatives.

The reduction of raised blood glucose levels by a compound of general formula I is demonstrated by the following experimental data. Male Swiss mice, weighing at least 30 grams, were fasted for 18-24 hours and a measured amount of a 0.6% solution of a compound of general formula I in a 0.5% aqueous methylcellulose solution was administered orally or intraperitoneally. After 15 minutes a 1 molar solution of L-alanine (pH 7.21) was injected intraperitoneally in an amount calculated to provide 0.1 ml/10 g body weight. After an additional 30 minutes, the mice were sacrificed and the blood collected. The serum was then analyzed for blood glucose according to standard laboratory methods and the blood glucose level of the animals given a test compound was compared with the blood glucose level of control animals given only L-alanine. A ratio representing the reduction of the L-alanine induced blood glucose increase due to administration of a test compound serves as a measure of effectiveness of the test compound. The percentage of serum glucose lowering is calculated according to the formula $$\% \text{ Serum Glucose Lowering} = \frac{(\text{alanine control}) - (\text{alkanaminium treated})}{(\text{alanine control}) - (\text{fasted control})} \times 100$$

wherein the quantities in parentheses represent serum glucose concentrations expressed in uniform units. Thus, a blood glucose level in a treated mouse identical to that of a fasted control would give a Serum Glucose Lowering of 100%. The results of tests of various doses of N-[3-(dimethylamino)-2-n-propoxy-2-propenylidene]-N-methylmethanaminium camsylate and of the corresponding perchlorate and iodide salts are tabulated below.

$$CH_3\diagdown_{CH_3}\!\!N-CH=\overset{\overset{\displaystyle OCH_2CH_2CH_3}{|}}{C}-CH=\overset{+}{N}\diagup^{CH_3}_{CH_3} \cdot An^-$$

| Dosage, mg/kg | Route of Administration | % Serum Glucose Lowering | | |
|---|---|---|---|---|
| | | Camsylate | Perchlorate | Iodide |
| 40 | oral | 178 | — | — |
| 30 | oral | 288 | — | — |
| 20 | oral | 122 | — | — |
| 15 | oral | 135 | — | — |
| 30 | i.p. | 314 | 234 | 201 |
| 15 | i.p. | 337 | 228 | 183 |
| 7.5 | i.p. | 220 | 140 | 129 |

Camsylate salts of formula I may be prepared by anion exchange from the corresponding salts of general formula Ia wherein An is an anion other than camsylate. In practice, the perchlorate salt is used most often in preparation of compounds of general formula Ia.

When a camsylate salt of general formula I is to be prepared, the compounds of formula Ia may be subjected to any suitable anion exchange method. For example, a commercially available anion exchange resin, for example, a column containing Dowex ® 1-8X resin, a polymeric resin manufactured by The Dow Chemical Company, may be washed with an aqueous solution of 10-camphorsulfonic acid and a solution of the perchlorate salt of general formula Ia in an aqueous solvent, for example, aqueous ethanol, poured through the resin. The eluted solution containing the camsylate salt of general formula I is concentrated by evaporation and recrystallized. Alternatively, the perchlorate salt of general formula Ia may be dissolved by heating in an appropriate anhydrous solvent, such as absolute alcohol, adding a concentrated aqueous solution of an alkali metal camsylate to the warm solution, and stirring to form a clear solution. The solution is sonified to ensure complete precipitation, additional anhydrous solvent is added, and the solution is cooled to precipitate alkali metal perchlorate salt, which is removed by filtration. The solution of the camsylate salt of general formula I is concentrated by evaporation and purified by art-recognized methods of extraction and recrystallation. A preferred method of anion exchange is to stir a solid methanaminium perchlorate salt of formula I with an alkali metal camsylsate salt for about 1 to 2 hours, using an excess, for example, from 1 to 2 mole equivalents, of the alkali metal camsylate. During stirring, water insoluble alkali metal perchlorate is precipitated and may be removed by filtration, leaving an aqueous solution of the camsylate salt formula I. The solution is extracted into a suitable solvent, for example, a chlorinated hydrocarbon such a methylene chloride, preferably after addition of an additional amount, for example, 1 equivalent, of the alkali metal camsylate. The extract is then dried and recrystallized from an appropriate solvent.

Compounds of formula I, prepared according to the methods disclosed hereinabove, may be purified by art-recognized methods, especially by recrystallization from a suitable solvent or from a combination of solvents. Suitable solvents for the recrystallization of a compound of formula I include alcohols, such as methanol, ethanol and isopropanol; esters, such as ethylacetate; ketones, such as acetone or butanone; nitriles, such as acetonitrile; and mixtures of such solvents with water or with an aromatic hydrocarbon, such as toluene.

The perchlorate salts of general formula Ia are prepared by methods disclosed in co-pending application U.S. Ser. No. 494,741 and in the prior art.

General methods suitable for preparing compounds of formula Ia wherein R is $OR^2$ have been described in the prior art, for example, by Z. Arnold, *Collection Czech. Commun.*, 38, 1168–72 (1973), which is incorporated herein by reference. Compounds of formula Ia wherein R is $R^2O$ are prepared by reacting a mixed acetal of formula II with a Vilsmeier-Haack reagent and quenching the reaction with aqueous sodium perchlorate, as shown in Reaction Scheme A.

Reaction Scheme A

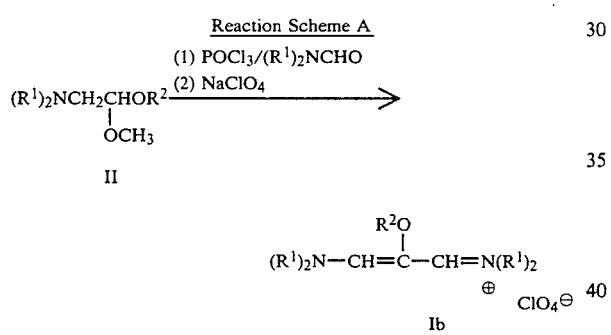

In Reaction Scheme A, $R^1$ and $R^2$ have the meanings defined above.

General methods for performing the Vilsmeier-Haack reaction are well known to the prior art. For the preparation of the compounds of general formula Ib, phosphoryl chloride is added to the dialkylformamide and the mixed acetal of formula II added gradually, maintaining a temperature during addition of about 90°–100° C. The product is then isolated by pouring the cooled solution into cooled aqueous solution of an appropriate salt, such as sodium perchlorate, to yield the perchlorate salt of formula Ib.

The mixed acetal of formula II may be prepared by methods analogous to those used for the preparation of previously known mixed acetals. For example, an alcohol of formula $R^2OH$ may be reacted with N-bromosuccinimide (NBS) and methyl vinyl ether in an appropriate solvent, for example, a chlorinated hydrocarbon such as carbon tetrachloride or methylene chloride, at a temperature of from about $-10°$ to $10°$ C., to produce a bromoethane acetal of the formula $BrCH_2CH(OCH_3)OR^2$. Upon completion of the reaction, as indicated by vapor phase chromatography, the reaction mixture is filtered and the solvent evaporated. The bromoethyl acetal is dissolved in an appropriate solvent, for example, dimethylformamide or ethyl ether, chilled to about $-10°$ to $10°$ C., and an excess, for example, 2 to 3 equivalents, of a dialkylamine of formula $NH(R^1)_2$ added with stirring. The reaction mixture is permitted to warm to ambient temperature and stirring is continued for from about 8 hours to about 10 days, until the reaction is complete. The resulting dialkylaminoethyl acetal of formula II is isolated by extraction into an appropriate solvent, for example, a hydrocarbon such as hexane, and evaporation of the solvent.

Where $R^1$ is methyl, the dialkylformamide of formula $(R^1)_2NCHO$ which is employed in the performance of the Vilsmeier-Haack reaction according to Reaction Scheme A is dimethylformamide. Compounds of formula Ia wherein $R^1$ is ethyl may be prepared by using diethylformamide for preparation of the Vilsmeier-Haack reagent or by refluxing a compound of formula Ia wherein $R^1$ is methyl with diethylamine and p-toluenesulfonic acid for from about 1 to about 4 hours in a suitable solvent, such as ethanol.

The novel compounds of general formula Ic, which are compounds of formula Ia wherein X is a divalent sulfur atom are prepared by reaction of an $R^2$-substituted sulfenyl bromide, with an appropriate dialkylaminoacrolein and subsequent reaction of the resulting 3-(dialkylamino)-2-($R^2$-thio)-2-propenal with an appropriate dialkylcarbamoyl halide, for example, a dialkylcarbamoyl chloride, and with a salt of the desired anion, as shown in Reaction Scheme B, wherein $R^1$ and $R^2$ have the meanings defined above.

Reaction Scheme B

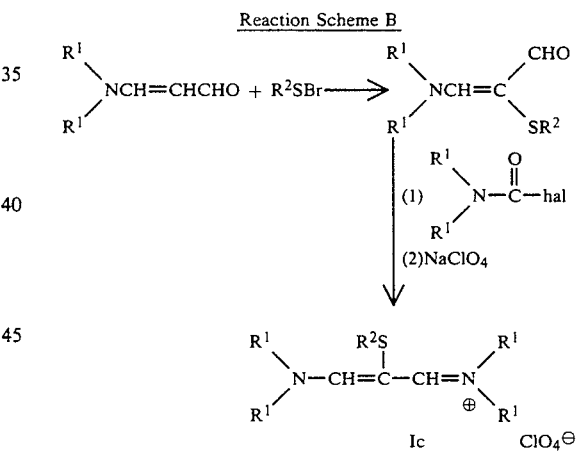

Dialkylaminoacroleins and dialkylcarbamoyl halides used as intermediates in the synthesis of compounds of formula Ic are well known and may be obtained from commercial sources or prepared by methods well known to the prior art.

$R^2$-Sulfenyl bromides of formula $R^2SBr$ are also well known to the prior art. For use as intermediates in the preparation of a compound of formula Ic, a compound for formula $R^2SBr$ is preferably generated in situ by reaction of an $R^2$-disulfide of formula $R^2SSR^2$ with bromine. Approximately one equivalent of bromine is added to the disulfide, which is dissolved in an appropriate solvent, for example, a chlorinated hydrocarbon such as methylene chloride, and reacted under an inert atmosphere, such as nitrogen or argon, at a reduced temperature, for example, from about $-10°$ to $10°$ C., for from about 5 to about 20 minutes.

Following the formation of the $R^2$-sulfenyl bromide, a solution of 3-dialkylaminoacrolein and a base, for example, an organic base such as triethylamine, in a suitable solvent, such as methylene chloride, is added gradually with continued cooling. When the exothermic reaction subsides, the reaction mixture is permitted to warm gradually to room temperature. The reaction mixture is then extracted with water and the organic layer concentrated to give crude 3-(dialkylamino)-2-($R^2$-thio)-2-propenal, which is then purified by standard methods, for example, by preparative high pressure liquid chromatography, using an appropriate solvent such as ethyl acetate.

The 3-(dialkylamino)-2-($R^2$-thio)-2-propenal is mixed with an excess of dialkylcarbamoyl halide in an appropriate organic solvent, for example, benzene, and stirred at room temperature for from about 1 to about 7 days. The reaction mixture is extracted with water and the aqueous layer charged with an excess of an inorganic salt, preferably sodium perchlorate, to yield a compound of formula Ic.

Methods for the preparation of compounds of general formula I and suitable compositions for the administration thereof are further illustrated by the following examples.

EXAMPLE 1

Preparation of bromoacetaldehyde methoxy propoxy acetal

N-Bromosuccinimide, 1000 g (5.6 mol), 1-propanol, 336 g (5.6 mol), and methylene chloride, 1000 ml, were placed in a 5 liter reaction flask equipped with mechanical stirrer, gas bubbler outlet, and a gas inlet tube. After cooling the mixture to $-10°$ C. in a dry ice-acetone bath, methyl vinyl ether, 450 g, (7.76 mol), was metered into the reaction flask at a rate such that almost none escaped through the bubbler outlet. The addition required 1½ hours. After addition was complete, the mixture was stirred for two hours at ambient temperature, was filtered to remove solids, and the filtrate was evaporated to yield bromoacetaldehyde methoxy propoxy acetal as a yellow oil, 937 g (85%).

NMR (CDCl$_3$): δ 4.5 (t, 1H), 3.35 (m, 7H), 1.6 (sex, 2H), 0.95 (t, 3H).

EXAMPLE 2

Preparation of dimethylaminoacetaldehyde methoxy propoxy acetal

A 12 liter flask equipped with mechanical stirrer, gas inlet tube, and Dewar condenser was charged with 2000 g (10.1 mol) of bromoacetaldehyde methoxy propoxy acetal and 6000 g of DMF. The solution was cooled to $-15°$ C. in a dry ice-acetone bath and dimethylamine, 1500 g (34 mol), was bubbled into the reaction mixture over a 2 hour period. A reaction temperature of $-10°$ to $-15°$ C. was maintained throughout the addition to prevent loss of dimethylamine from the solution. After addition was complete, the cooling bath was removed and the reaction mixture was allowed to warm slowly to ambient temperature.

The reaction was monitored by vapor phase chromatography. After 14 hours, the mixture contained 62% product and 38% starting material. An additional 300 g of dimethylamine were added and stirring was continued for 8 hours. At this time, analysis showed that the mixture contained greater than 95% product. The mixture was poured into an equal volume of water, and the aqueous solution was extracted with hexane. Evaporation of the hexane layer yielded dimethylaminoacetaldehyde methoxy propoxy acetal as a yellow oil, 1144 g, (70%). Its NMR spectrum was satisfactory and the product was used in the next step without further purification.

NMR (CDCl$_3$): δ4.5 (t, 1H), 3.3 (m, 5H), 2.3 (m, 8H), 1.6 (2H), 0.95 (t, 3H).

EXAMPLE 3

Preparation of N-(3-(dimethylamino)-2-(n-propoxy)-2-propenylidene)-N-methylmethanaminium perchlorate Dimethylformamide, 1250 ml (16.1 mol), was placed in a 12 l flask and phosphoryl chloride, 733 ml (8.0 mol), was added with stirring at a rate such that the reaction temperature reached 90° C. Dimethylaminoacetylaldehyde methoxy propoxy acetal, 650 g (4.0 mol), was slowly dripped into the mixture. A heavy white vapor formed in the airspace above the solution during the addition, and the flask was purged periodically with nitrogen to allow visual inspection of the reaction mixture. By a combination of adjustment of the rate of addition and intermittent cooling of the reaction mixture with an ice bath, the reaction temperature was maintained between 90° and 100° C. The addition was complete in 40 minutes. The reaction remained totally under control throughout the addition, and there was no delayed exothermic reaction after the addition was complete. The mixture was stirred for 1 hour at 90° C., then allowed to cool. The black mixture was poured over 2500 g of ice with stirring. A solution of sodium perchlorate, 1100 g in 1500 ml of water was added and, after approximately 30 seconds, the solution turned into a heavy slush. Filtration of this mixture followed by several ice water washings yielded 630 g (55%) of N-(3-(dimethylamino)-2-(n-propoxy)-2-propenylidene)-N-methylmethanaminium perchlorate as a fluffy tan solid. M.p. 119°–120° C.

EXAMPLE 4

Preparation of N-[3-(dimethylamino)-2-(n-propoxy)-2-propenylidene]-N-methylmethanaminium camsylate Five (5) g (0.017 mol) of the product of Example 3 was dissolved in 4 ml of absolute alcohol by warming on a water-bath to 70° C. Five (5) g (0.0185 mol) of potassium camsylate was dissolved in 4 ml of water, warmed to 70° C. and added to the perchlorate solution while warm (60° C.), stirring until a clear solution resulted. The solution was sonified for 15 minutes to assure the complete precipitation of potassium perchlorate. Another portion of 20 ml absolute alcohol was added and the content placed in a refrigerator overnight. The potassium perchlorate was filtered off with suction and the filtrate concentrated to dryness on a water bath. The solids were extracted with methylene chloride and filtered, and the solution concentrated to dryness. The residue was extracted with ethyl acetate, and the solution cooled and filtered to yield N-[3-(dimethylamino)-2-(n-propoxy)-2-propenylidene]-N-methylmethanaminium camsylate as leafy crystalline solids (yield 71; %). M.p. 187° C.

EXAMPLE 5

Preparation of
N-(3-(dimethylamino)-2-(phenylthio)-2-propenylidene)-
N-methylmethanaminium perchlorate A methylene chloride solution of 32.75 g (0.15 mol) phenyl disulfide was cooled to 0° C. under nitrogen and 23.9 g (0.15 mol) bromine was added neat. After 10 minutes a solution of 50 ml triethylamine, 100 ml methylene chloride and 25 g (0.25 mol) 3-dimethylaminoacrolein (Fluka Chem. Co.) was added dropwise with cooling to hold the temperature at 0° C. The reaction was allowed to warm to room temperature overnight, shaken with 200 ml water (2×), and the organic layer dried ($Na_2SO_4$) and concentrated to give 49.5 g crude 3-(dimethylamino)-2-(phenylthio)-2-propenal. This aldehyde was purified by preparative HPLC (EtOAc) to give 20.2 g pure aldehyde.

A 17.5 g (0.085 mol) sample of 3-(dimethylamino)-2-(phenylthio)-2-propenal was mixed with 10.7 g (0.1 mol) dimethylcarbamyl chloride and 60 ml benzene. The reaction was stirred at room temperature for 3 days and extracted with 100 ml water. The aqueous layer was charged with 15 g $NaClO_4 \cdot H_2O$ and the precipitate collected and dried. After recrystallization (1:1 $CH_3OH/C_2H_5OH$), 9.5 g (49%) N-(3-(dimethylamino)-2-phenylthio)-2-propenylidine-N-methylmethaminium perchlorate was obtained as a light orange solid. M.p. 134°–136° C.

EXAMPLE 6

Preparation of
N-(3-(dimethylamino)-2-(phenylthio)-2-propenylidene)-
N-methylmethanaminium camsylate When, in the procedure of Example 4, the product of Example 5 is substituted for N-(3-(dimethylamino)-2-(n-propoxy)-2-propenylidene)-N-methylmethanaminium perchlorate, the title compound is obtained.

EXAMPLE 7

Direct Compression Tabletting

| Ingredient | % Of Composition | mg per Tablet |
|---|---|---|
| N—[3-(Dimethylamino)-2-(n-propoxy)-2-propenylidene]-N—methylmethanaminium camsylate | 30.0 | 100.00 |
| Micronized cellulose pH 102 | 30.0 | 83.35 |
| Lactose, anhydrous | 42.5 | 141.65 |
| Magnesium Stearate | 2.0 | 6.65 |
| Cab-O-Sil ® (silica) | 0.5 | 1.65 |
| TOTAL | 100.0 | 333.30 |

All ingredients except the magnesium stearate are blended for 25 minutes. The magnesium stearate is screened and blended with the mixture for an additional 5 minutes, and the mixture compressed to form 13/32 inch tablets.

EXAMPLE 8

Preparation of Tablets by Wet Granulation

| Ingredient | % Of Composition | mg per Tablet |
|---|---|---|
| N—[3-(Dimethylamino)-2-(n-propoxy)-2-propenylidene]-N—methylmethanaminium camsylate | 85.0 | 500.00 |
| Starch | 1.7 | 10.0 |
| Polyvinylpyrrolidone (8% Alcohol Solution) | 2.4 | 14.0 |
| Micronized cellulose pH 101 | 10.2 | 60.0 |
| Magnesium Stearate | 0.7 | 4.0 |
| TOTAL | 100.0 | 588.0 |

The camsylate salt and starch are mixed together and granulated with the alcoholic PVP solution. The wet mass is passed through a 12 mesh screen and dried at 120° C. The dried granulation is passed through a 16 mesh screen and mixed with the micronized cellulose and magnesium stearate, which have previously been screened through a 40 mesh screen. The mixture is compressed into 7/16 inch tablets.

I claim:

1. A compound of the formula

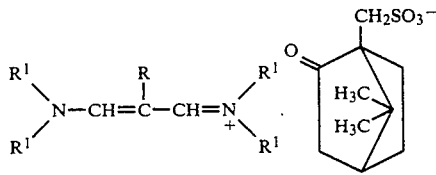

wherein R represents a group of formula $R^2X$; $R^1$ represents methyl or ethyl; $R^2$ represents straight or branched alkyl of from 1 to 12 carbon atoms, straight or branched alkenyl of from 2 to 12 carbon atoms, cycloalkyl of from 3 to 8 carbon atoms, cycloalkylalkyl of from 4 to 10 carbon atoms, phenyl or benzyl; and X is an oxygen atom or a divalent sulfur atom.

2. A compound of claim 1 wherein R is $R^2O$, and $R^1$ and $R^2$ have the meanings defined in claim 1.

3. The compound of claim 2 which is N-[3-(dimethylamino)-2-(n-propoxy)-2-propenylidene]-N-methylmethanaminium camsylate.

4. A compound of claim 1 wherein R is $R^2S$, and $R^1$ and $R^2$ have the meanings defined in claim 1.

* * * * *